(12) United States Patent
Ohmori et al.

(10) Patent No.: US 6,678,397 B1
(45) Date of Patent: Jan. 13, 2004

(54) MEDICAL IMAGE FILING SYSTEM

(75) Inventors: Shinichi Ohmori, Hachioji (JP); Keiichi Hiyama, Hino (JP); Tatsuya Shiobara, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/491,470

(22) Filed: Jan. 26, 2000

(30) Foreign Application Priority Data

Jan. 26, 1999 (JP) .......................................... 11-017592

(51) Int. Cl.$^7$ .......................... G06K 9/60; G06F 3/023; G06F 3/06; G11B 5/86; G11B 15/52
(52) U.S. Cl. ..................... 382/128; 382/305; 369/47.12; 345/748; 710/39
(58) Field of Search ........................ 710/39; 369/47.12; 345/748, 749; 382/305, 128, 132; 379/209.01; 348/231.2

(56) References Cited

U.S. PATENT DOCUMENTS

| 4,642,758 A | * | 2/1987 | Teng ............................ 707/10 |
| 5,019,975 A | * | 5/1991 | Mukai ............................ 707/7 |

(List continued on next page.)

FOREIGN PATENT DOCUMENTS

| JP | 62-209670 | | 9/1987 | |
| JP | 63-008868 | * | 1/1988 | |
| JP | 01044578 A | * | 2/1989 | ........... G06F/15/40 |
| JP | 02-167131 | * | 6/1990 | |
| JP | 04253273 A | * | 9/1992 | ........... G06F/15/40 |
| JP | 07-044578 | * | 2/1995 | |
| JP | 08241354 A | * | 9/1996 | ........... G06F/19/00 |
| JP | 10-143402 | * | 5/1998 | |

OTHER PUBLICATIONS

Galitz, Wilbert O., The essential guide to user interface design: an introduction to GUI design principles and techniques, Wiley Computer Publishing, 1997, pp. 542–545.*
Hartley, Tim, GUI design fundamentals, Computer Prep, 1998, p. 11.*
English Abstract for JP 01044578 A.*
English Abstract for JP 04253273 A.*
English Abstract and Machine Translation for JP 08241354 A.*

Primary Examiner—Bhavesh M. Mehta
Assistant Examiner—Christopher Sukhaphadhana
(74) Attorney, Agent, or Firm—Scully, Scott, Murphy & Presser

(57) ABSTRACT

A medical image filing system having a first recording device for recording a plurality of image data from a medical image pickup device; a second recording device for recording the plurality of image data from the medical image pickup device, the second recording device has a recording speed slower and a recording capacity greater than that of the first recording device; and at least one image reproducing device for reading and reproducing designated image data from the plurality of image data recorded in the first and second recording devices. The at least one image reproducing device has a third recording device for recording the designated image data, wherein the designated image data recorded in the third recording device can also be reproduced by the at least one reproducing device. The at least one reproducing device further has apparatus or software to designate the image data recorded in the second recording device and designate either of the first or third recording devices to copy the designated image data from the second recording device to the designated first or third recording devices. A computer readable program code means for reproducing the plurality of image data in the medical image filing system is also provided.

22 Claims, 14 Drawing Sheets

U.S. PATENT DOCUMENTS

| | | | | |
|---|---|---|---|---|
| 5,029,016 A | * | 7/1991 | Hiyama et al. | 348/74 |
| 5,321,520 A | * | 6/1994 | Inga et al. | 358/1.9 |
| 5,463,754 A | * | 10/1995 | Beausoleil et al. | 707/200 |
| 5,469,353 A | * | 11/1995 | Pinsky et al. | 382/131 |
| 5,586,262 A | * | 12/1996 | Komatsu et al. | 705/2 |
| 5,701,513 A | * | 12/1997 | Kaneko | 710/119 |
| 5,754,887 A | * | 5/1998 | Damron et al. | 710/117 |
| 6,006,191 A | * | 12/1999 | DiRienzo | 705/2 |
| 6,170,042 B1 | * | 1/2001 | Gaertner et al. | 709/103 |
| 6,219,669 B1 | * | 4/2001 | Haff et al. | 707/10 |
| 6,430,281 B1 | * | 8/2002 | Morley et al. | 379/202.01 |
| 6,526,304 B1 | * | 2/2003 | Patel et al. | 600/407 |

* cited by examiner

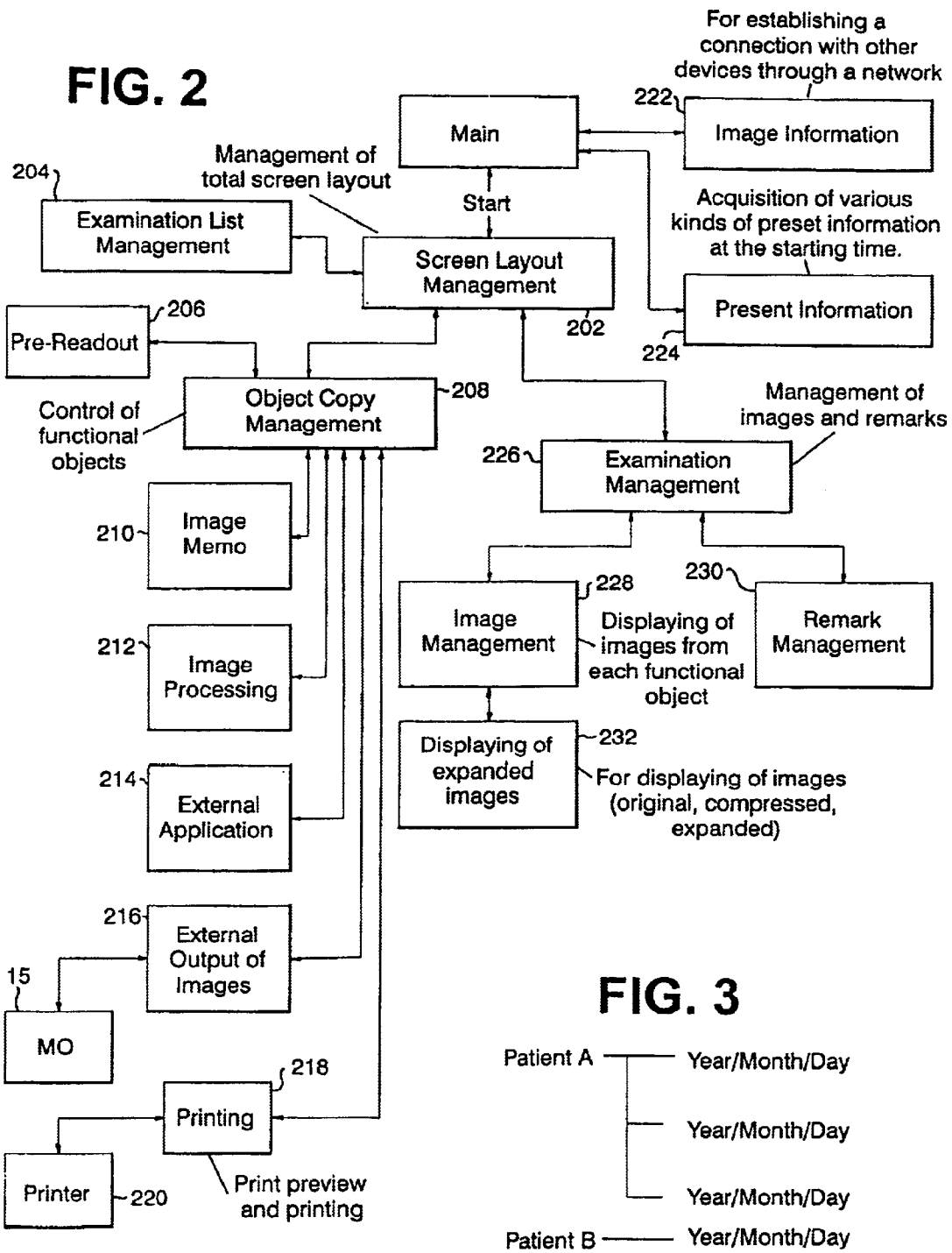

FIG. 6

| | | | | |
|---|---|---|---|---|
| | Small-Capacity Storage Device | ▼ | | |

| M/F | Patient ID | Patient Name | Examination |
|---|---|---|---|
| M | 00-571-28 | K.M. | |
| M | 11-156-61 | Y.K. | |
| M | 11-156-61 | Y.K. | |
| M | 60-577-68 | Y.K. | |
| M | 00-373-83 | O.Y. | |
| M | 07-249-88 | O.T. | |
| M | 11-544-22 | N.T. | |
| M | 11-544-22 | N.T. | |
| M | 08-724-52 | K.S. | |
| M | 01-385-13 | S.Y. | |
| M | 18-757-32 | T.Y. | |
| M | 18-260-64 | H.T. | |
| M | 19-162-16 | T.K. | |
| M | 19-201-21 | O.M. | |
| F | 19-238-14 | S.H. | |

Drag and Drop

A: Patient ID ▼ *

| EXE | Image Memo | MO bitmap | MO jpeg | MO gif | FD bitmap |
|---|---|---|---|---|---|
| FD jpeg | 4-Part Split Image | Printing | Printing of Remarks and Images | Highlight Processing | Pre-Readout Registration |

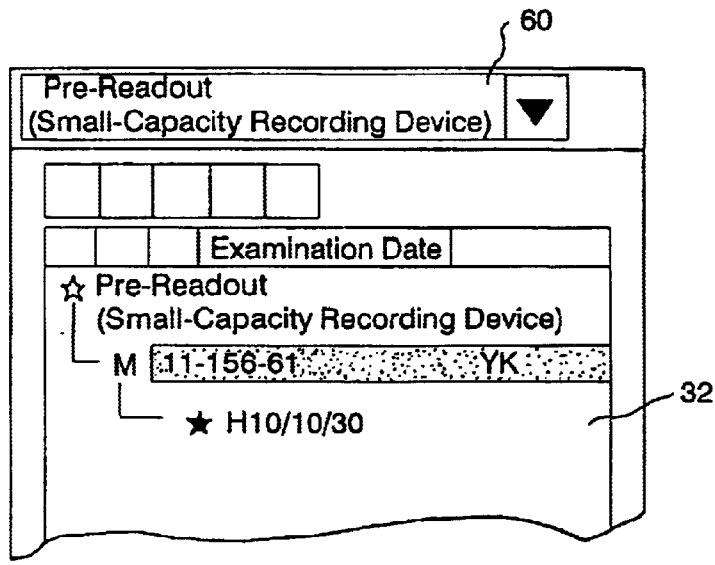
FIG. 19
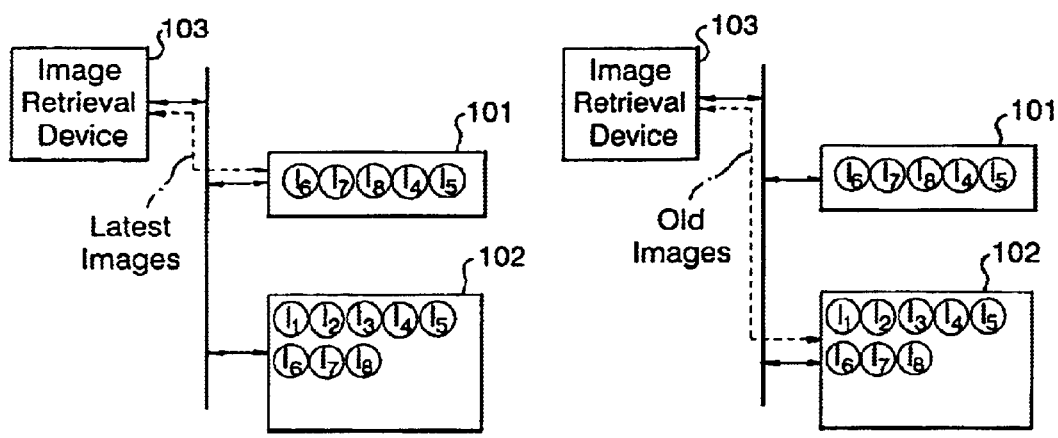
**FIG. 20(a)
(Prior Art)**
**FIG. 20(b)
(Prior Art)**

MEDICAL IMAGE FILING SYSTEM

BACKGROUND OF THE INVENTION

1. Field of the Invention

This invention relates to a medical image filing system, more specifically to a medical image filing system which has some characteristics in the reading part of recorded image data.

2. Prior Art

In recent years, a video-endoscope equipped with a Charge Coupled Device (CCD) at its distal end as an image-capture means has become popular instead of a fiberscope which observes a body cavity, using an image guide formed by optical fibers.

Therefore, a medium to record a photographed or electronically captured endoscopic image of a body cavity has been changing from an analog-recording medium to digital recording media, such as a hard disk, a floppy disk, an optical disk, and a magneto-optical (MO) disk.

In a conventional recording and reproducing system or image filing system for endoscopic image data, an image input means consisting of a video-endoscope, etc. captures and compresses an endoscopic image, and then an image recording means such as a hard disk records it. Also, a recording means with sufficiently large capacity, comparing to a hard disk, has been proposed. For example, an image filing system consisting of an auto-changer type MO recording means with several MO disks which automatically changes to another MO disk when one MO disk becomes full.

In the conventional image filing systems mentioned above, when performing endoscopic examination, generally, patient data such as a patient ID, name, birth date, and sex, is input into a video-endoscope by using a keyboard, etc. The input patient data and patient endoscopic images are compressed and recorded in the above image recording means or large-capacity image recording means via a Local Area Network (hereafter LAN), etc.

Also, after the examination, by using an image search means, it is possible to search some patient data such as a certain patient's past endoscopic images from an image recording means, for example, to observe the change of a lesion. This leads to efficient diagnosis and treatment.

As shown in FIG. 20(a), an image filing system of the prior art is shown. The image filing system is equipped with an image recording means or a large-capacity image recording means which records, an identical compressed endoscopic image $I_n$ in both the image recording means 101 and a large-capacity image recording means 102, respectively. In the figure, the most current or newest image is designated with the highest number. The image recording means 101 is accessed by the image search means (image retrieval device) 103 to search and reproduce desired image data.

However, a problem occurs in the above process. As the recording capacity of the image recording means 101 is small in comparison with the large-capacity image recording means 102, image recording means 101 can record fewer image data than the large-capacity image recording means 102 can. Therefore, as shown in FIG. 20(b), in the image recording means 101, when the recording area for new image data becomes full, new image data are written over the oldest image data. In other words, the oldest image data is erased to record the newest image data. On the other hand, in the large-capacity image recording means 102, since a recording area is sufficiently secured, image data can be recorded (added to the old data). Furthermore, the image recording means 102 is accessed by the image search means 103 to search and reproduce desired image data.

The data access speed for a MO recording means consisting of the large-capacity image recording means 102 is slow in comparison with the data access speed of the hard disk device consisting of the image recording means 101. Therefore, when the newest image data are recorded by writing over the oldest data, and old endoscopic images are searched, data in the large-capacity image recording means 102 need to be searched. Because, old data remains only in the large-capacity image recording means 102. Accordingly, searching data in the large-capacity image recording means 102 takes a long time.

SUMMARY OF THE INVENTION

Therefore it is an object of the present invention to provide a medical image filing system which reduces time to search and reproduce image data stored in a large-capacity image recording device.

Accordingly, a medical image filing system is provided. The medical image filing system of the present invention comprises: a first recording device for recording a plurality of image data from a medical image pickup means; a second recording device for recording said plurality of image data from the medical image pickup means, the second recording device having a recording speed slower and a recording capacity greater than that of the first recording device; and at least one image reproducing device for reading and reproducing designated image data from the plurality of image data recorded in the first and second recording devices. The at least one image reproducing device having a third recording device for recording the designated image data. Wherein the designated image data recorded in the third recording device can also be reproduced by the at least one reproducing device. The at least one reproducing device further having designating means to designate the image data recorded in the second recording device and designate either of the first or third recording devices to copy the designated image data from the second recording device to the designated first or third recording devices.

Also provided is a computer program product embodied in a computer-readable medium for reproducing a plurality of image data in a medical image filing system. The medical image filing system having first and second recording devices for recording the plurality of image data from a medical image pickup means. The second recording device having a recording speed slower and a recording capacity greater than that of the first recording device. The computer program product comprising: computer readable program code means for designating at least one image data from the plurality of image data recorded in the second recording device; computer readable program code means for designating either of the first or a third recording device of an image reproducing device for copying of the at least one designated image data from the second recording device to the designated first or third recording device; and computer readable program code means for copying the at least one designated image data from the second recording device to the designated first or third recording device.

In a preferred implementation of the system and software product of the present invention, a plurality of image reproducing devices is provided which are connected to each other by a network means, such as a Local Area Network (LAN).

In another preferred implementation of the system and software product of the present invention, the copying of the designated image data from the second recording device to the designated first or third recording device can be delayed when there exists a simultaneous copying of any of the plurality of image data from the second recording device to either the first or third recording devices.

In another preferred implementation of the system and software product, of the present invention the copying of the designated image data from the second recording device to the designated first or third recording device can be restarted after the simultaneous copying of any of the plurality of image data from the second recording device to either the first or third recording devices is completed. The restarting means can comprise a manual indication to the image reproducing device or an automatic indication to the image reproducing device after a lapse of a preset time.

In another preferred implementation of the system and software product, of the present invention a day and time to copy the designated image data in the second recording device to the designated first or third recording device can be designated in advance of the time that the designated image data will be used.

In another preferred implementation of the system and software product of the present invention, where the system or method comprises a plurality of image reproducing devices and where a designated image is designated to be simultaneously copied to more than one of the third recording devices, the copying of the designated image data from the second recording device to all but one of the third recording devices can be stopped and restarted after the copying to the one third recording device is completed. The restarting means can comprises a manual indication to the image reproducing device or an automatic indication to the image reproducing device after a lapse of a preset time.

In another preferred implementation of the system and software product of the present invention, a day and a time when copying is to be performed can be designated by a user.

In yet another preferred implementation of the system and software product of the present invention, when the image data is designated to be used on a certain day, the copying is performed on a previous day.

In still yet another preferred implementation of the system and software product of the present invention wherein there are a plurality of image reproducing devices, the designation of the same image data to be copied during the same time to the same of the first or third recording devices can be prohibited to avoid conflicts.

The medical image filing system in this invention can make it possible to reduce the time to search and reproduce image data stored in the second large-capacity recording device, as follows. The image reproducing device can reproduce the image data mentioned above recorded in the third recording device. Appoint the image data recorded in the second recording device, and copy them to either the first recording device or the third recording device, which a user can designate. In this way, by accessing the second recording device, and copying and storing the desired image data searched from the second recording device to and in the third recording device, it is possible to overcome the aforementioned problems of the prior art.

BRIEF DESCRIPTION OF THE DRAWINGS

These and other features, aspects, and advantages of the software product and apparatus of the present invention will become better understood with regard to the following description, appended claims, and accompanying drawings where:

FIG. 2 is a functional-block diagram showing the functions of the image reproducing means of FIG. 1.

FIG. 3 is a first diagram illustrating a database constructed in the controller of FIG. 1.

FIG. 6 is a diagram showing a first display example of the image displayed on the PC monitor of FIG. 1.

FIG. 9 is a diagram showing a first example of an image displayed on the PC monitor at the time of a registration process to read image data beforehand shown in FIG. 8.

FIG. 19 is a diagram showing an example of an image displayed on the PC monitor when image data read through the process of reading beforehand of FIG. 15 are reproduced.

FIGS. 20(*a*) and 20(*b*) illustrate an image filing system of the prior art.

DETAILED DESCRIPTION OF THE PREFERRED EMBODIMENT

Implementation of the present invention is not specific to any particular hardware system and may in fact be implemented by a number of software schemes. As a specific best mode example, however, the following is given.

Figure 1:
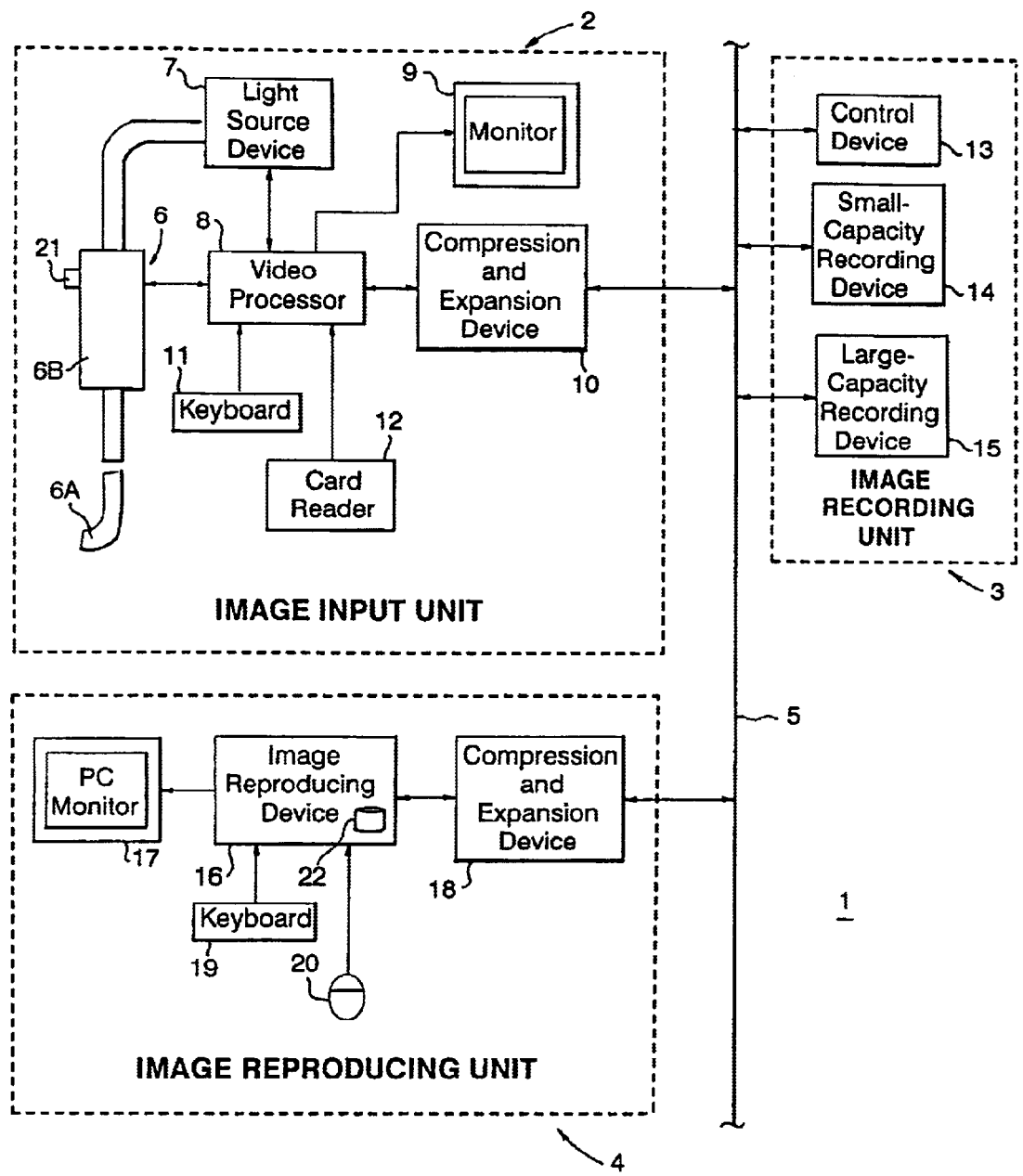
FIG. 1 is a diagram showing the construction of the medical image filing system of the present invention.

As shown in FIG. 1, the medical image filing system of the present invention, generally referred to by reference numeral 1, comprises an image input unit 2 which inputs images, an image recording unit 3 which records the input images, and an image reproducing unit 4 which searches and reproduces the recorded images. These units 2, 3, and 4 are mutually connected by a Local Area Network (LAN) 5, a network.

The image input unit 2 comprises a video-endoscope (also called a videoscope) 6 having a light guide and a built-in CCD, a light source 7 which supplies an illumination light to the light guide of the video-endoscope 6, a video-processor 8 which processes the signal of the CCD in the video-endoscope 6, a first monitor 9 which displays the video signal output from the video-processor 8, a first compressing and expanding device 10 which compresses and expands an image, a first keyboard 11 for inputting data, etc. to the video-processor 8, a card reader 12 which reads data such as those recorded in a patient card (not illustrated) which a patient owns, and inputs the data to the video-processor 8. The video-endoscope 6, the light source device 7, the first monitor 9, the first compressing and expanding device 10, the first keyboard 11, and the card reader 12 are connected with the video processor 8 by signal lines respectively.

The image recording unit 3 comprises a controller 13, a small-capacity recording device 14 with relatively small capacity, consisting of a hard disk, etc., and a large-capacity recording device 15 which includes an auto-changer type magneto-optical (MO) recording device with several magneto-optical disks which has a recording capacity much larger than that of the small-capacity recording device 14. Each device is connected via the LAN 5. The controller 13 monitors the condition of each unit 2, 3, and 4, and controls the small-capacity recording device 14 and the large-capacity recording device 15 to store a patient's image data in the small capacity recording device 14 and the large-capacity recording device 15.

The image reproducing unit 4 comprises an image reproducing device 16 which searches and reproduces an image, and preferably has the functions shown in FIG. 2, a second PC monitor 17 which displays a searched image, a second compressing and expanding device 18 which compresses and expands images, a second keyboard 19 for inputting data and commands to the image reproducing device 16, and a mouse 20. Each of the second PC monitor 17, the second compressing and reproducing device 18, the second keyboard 19, and the mouse 20 are connected with the image reproducing device 16 by signal lines.

The image input unit 2 and the image reproducing unit 4 are connected with the LAN 5 by the first and second compressing and expanding devices 10 and 18, respectively.

In addition, the video-endoscope 6 in the image input unit 2 has a long and thin insertion portion 6A, and a control section 6B placed at the proximal end of the insertion portion 6A. A release switch 21 for releasing an image is provided in the control section 6B. As relevant information, several database files (a patient database file, an examination database file, an image database file, etc.) are recorded by the controller 13 in the image recording unit 3. Table 1 and 2 show examples of recorded database files.

TABLE 1

| Patient ID | Patient Name | Sex | Birth Date | Comments |
|---|---|---|---|---|
| 1 | Taro Olympus | M | Feb. 19, 1973 | — |
| 2 | Hanako Olympus | F | Nov. 08, 1969 | — |
| . | . | . | . | . |
| . | . | . | . | . |
| . | . | . | . | . |

TABLE 2

| Examination ID | Examination Date | Patient ID | Biopsy | Department of Medical Examination | ... |
|---|---|---|---|---|---|
| 1240 | Feb. 14, 1995 | 2 | None | First Surgical Department | ... |
| 1241 | Feb. 14, 1995 | 1 | Done | Second Surgical Department | ... |
| . | . | . | . | . | . |
| . | . | . | . | . | . |
| . | . | . | . | . | . |

Table 1 is a patient database file. The data of each patient who has undergone an examination is recorded. "Patient ID" is an identifying number given to each patient to identify them. A certain patient can be specified by this "patient ID", "patient name", or "birth date" etc.

Table 2 is an examination database file. Data is recorded for each examination for a certain patient. "Examination ID" is given to each examination in the order of its performance. Examination can be specified by this "examination ID", an "examination date", and a "department of medical examination" etc. Other items can also be considered as examination data besides those shown in Table 2. Some examples of such are: Patient age at the time of examination; comments on examination; type of examination; hospitalization; outpatients; type of endoscope used; doctor name who performed examination; name of diseased part; diagnosis name; biopsy number; details of diagnosis; biopsy result; special examination; a type of a film; a film number; and a film location.

These patient data files and examination data files are used as a key to identify a patient. The related correspondence of the several inspection data are performed for a patient, and they are recorded.

Also, endoscopic images are recorded with corresponding examination data. Thus, since patient data, examination data, and image data are recorded, and all are related to each other, it is possible to search all desired information from one piece of the desired information.

FIG. 3 shows, generally, for a Patient A, various examinations such as a routine medical checkup, follow-up examination, reexamination, different types of examination, etc. which are performed for a patient.

Figure 4:
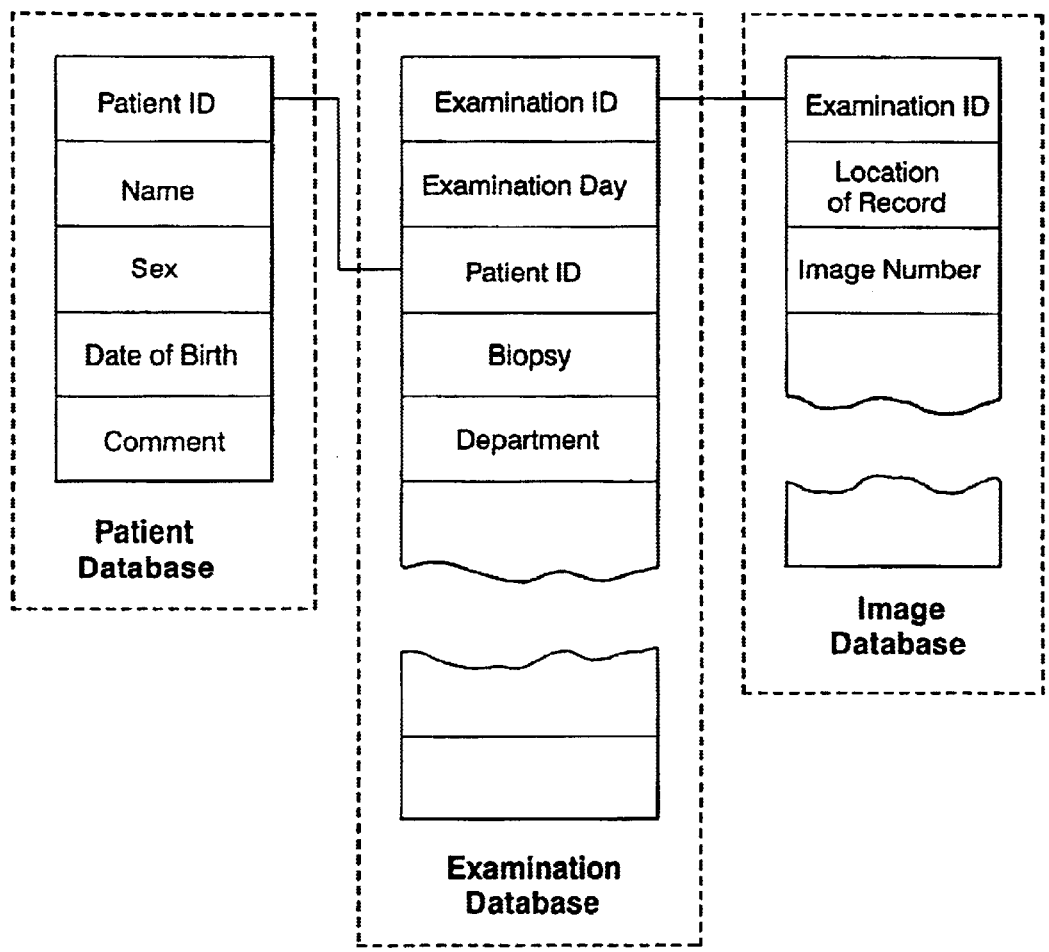
FIG. 4 is a second diagram illustrating a database constructed in the controller of FIG. 1.

FIG. 4 shows, a patient database file and an examination data file linked with a patient ID. Also, an examination database file and an image database file are linked with a patient ID. By creating database in this way, it is possible to search all desired information including image data from a single piece of the desired information.

The operation of the medical image filing system of the present invention will now be described. The outline of the basic operation in the entire medical image filing system 1 is explained with regard to FIG. 1 as follows. The medical image filing system 1 has an endoscopy function by the video-endoscope 6, a function to record captured endoscopic images, function to search and display the recorded images.

The image input unit 2 captures an endoscopic image by depressing release button 21, the image recording unit 3 records the captured image, and the image reproducing unit 4 searches and displays the recorded image. These three units 2, 3, and 4 are connected via LAN 5. Transmitting and receiving image data necessary to record, search, and display an image is performed between each unit while the controller 13 monitors the condition of these three units 2, 3, and 4 via LAN 5.

Furthermore, it is possible to connect and operate more than one image input unit 2 and image reproducing unit 4 to one image recording unit 3 via LAN 5. Thus, recording, searching, and displaying an image can be performed instantly at several different places.

The following is a detailed explanation of the image reproducing device 16. The power supply of each device of the image reproducing unit 4 is centralized. When turning on the power supply of the image reproducing unit 4, the power supply of the image reproducing device 16 is turned on. When the power supply of the image reproducing device 16 is turned on, a window is displayed on the second PC monitor 17.

Figure 5:
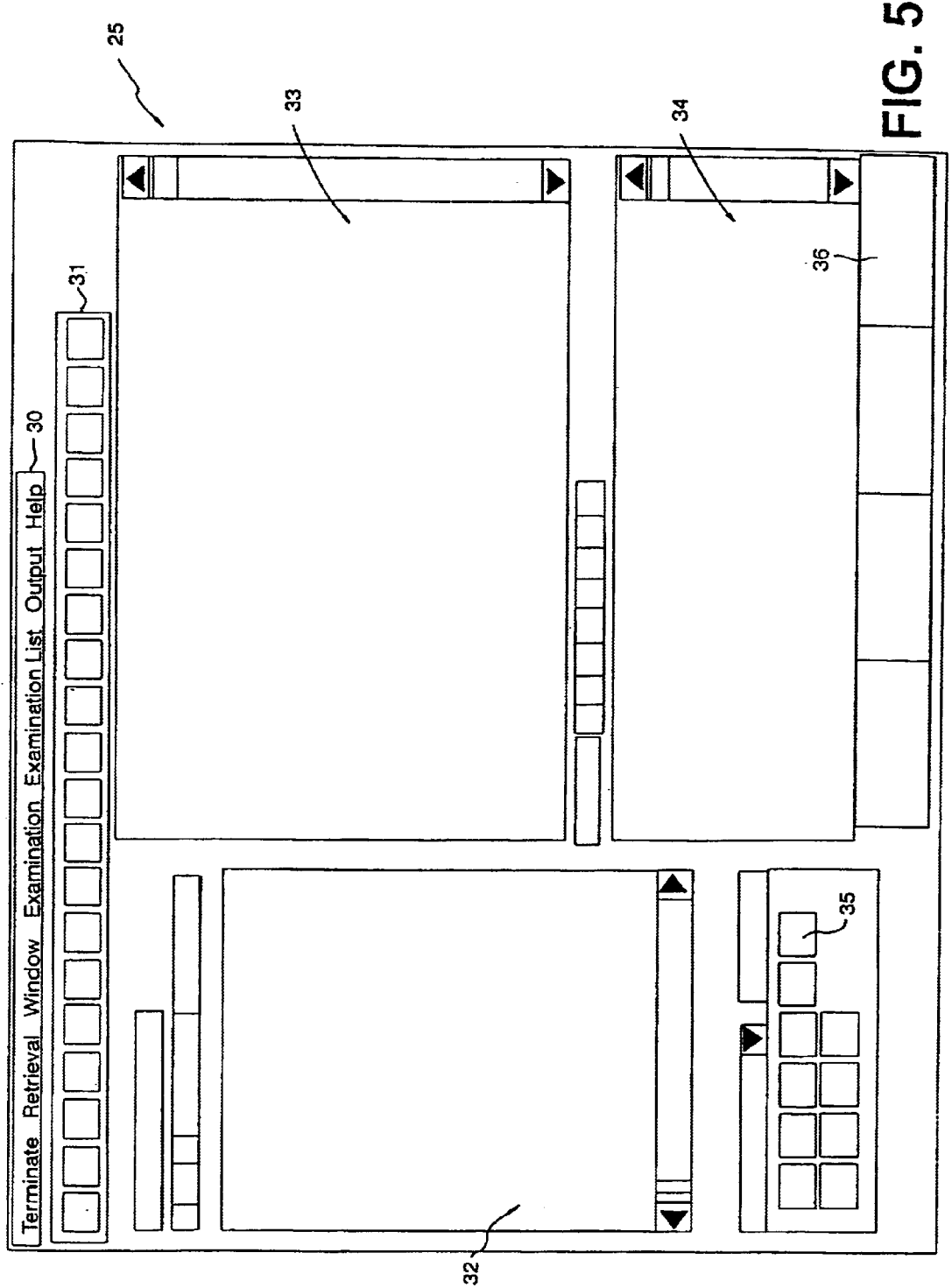
FIG. 5 is a block diagram showing image construction displayed on the PC monitor of FIG. 1.

The application software of the image reproducing device 16 is executed by inputting a specified user name and password to this window, after which, a main screen 25 is displayed, as shown in FIG. 5. Preferably, if a specified user name and a password are not input, the device does not work. Therefore, a third person can be prevented from illegally using the device or damaging data. Moreover, several different user levels can be set up. Therefore, it is possible to control user levels by dividing those users who can only view data, from those users who can view and change data. The application software can be resident on a semi-conductor chip in the image reproducing device 16, in a memory storage device in the image reproducing device 16, or in any manner known in the art.

As shown in FIG. 5, the main screen 25 displayed on the second PC monitor 17 connected to the image reproducing device 16 mainly consists of six areas: a menu bar 30 and a tool bar 31, an examination list display area 32, an image display area 33, a medical description display area 34, an object copy area 35, and a status bar 36. The role of these areas are explained below. In addition, each area has an independent function as a window.

Menu bar 30 is a function menu prepared in the image reproducing device 16 and tool bar 31 is a menu displayed with icons. Functions such as ending an operation of the image reproducing device 16, executing a search, modifying a display layout, saving input medical description data, customizing items, etc. are available on the menu bar 30 and tool bar 31.

At the Examination list display area 32 (examination list management 204 in FIG. 2), search conditions of examinations are displayed and can be selected, search is executed, and the result of the search is displayed. At the image display area 33 (image management 228 in FIG. 2), an index image of the searched images are displayed.

In the Medical description display area 34 (examination management 226 in FIG. 2), medical description information on examination is displayed. Inputting data is also possible in the medical description display area 34. The input data is recorded in the image recording unit 3, being related to a desired image. This input data acts as a keyword to search an image.

In the object copy area 35 (object copy management 208 in FIG. 2), delivering and receiving image data and medical description data to and from each function is prepared. Each function is displayed by an icon. By dragging and dropping an image or medical description to and on the icon, delivering and receiving data from and to each function module is instructed and executed. Function modules such as the following (from (a) to (f)) are available:

(a) Image memorandum function (image memo 210 in FIG. 2). The image memorandum function copies a selected image to a specified folder in a memory storage device 22 of the image reproducing device, and saves it temporarily. In the case where the application software for the image reproducing device 16 is stored in a memory storage device, this storage device can also comprise memory storage device 22.

(b) Image external output function (external output of images 216 in FIG. 2). The image external output function copies image data to external recording media such as a magneto-optical disk 15 connected to the image reproducing device. When copying, image data is first converted to a designated data format (a bit-map format, JPEG format, etc.).

(c) Printing function (printing 218 in FIG. 2). The printing function prints out image data and medical description data to printer 220 connected to the image reproducing device 16. When printing an image, images chosen from an image reproduction area can be displayed side by side as a preview.

(d) Image processing function (image processing 212 in FIG. 2). The image processing function displays the image chosen from image reproduction area after performing specified image processing.

(e) External application starter function (external application 214 in FIG. 2). When Application software such as word-processor software, spreadsheet software, slide production software, editor, etc. are installed to the image reproducing device, designated application software can be executed by using this icon.

(f) Reading out beforehand function (pre-readout 206 in FIG. 2). The reading out beforehand function designates a desired examination result, and reads it out beforehand to either the small-capacity recording device 14 or the image reproducing device 16. Thus, searching and reproducing an image stored in the large-capacity recording device 15 which has a slow search and reproduction speed becomes smooth.

In addition to these functions, the image reproducing device 16 may also have a screen layout management function 202 for management of the total screen layout, an image information function 222 for establishing a connection with other devices through a network, a preset information function 224 for acquisition of various kinds of preset information at the software's starting time, a remark management function 230 for management of image remarks, and a display of expanded images function 232 for displaying of images from original, compressed or expanded formats.

The Status bar 36 displays the process situation of the device, the number of examination hits by search, and the number of images.

Figure 6:
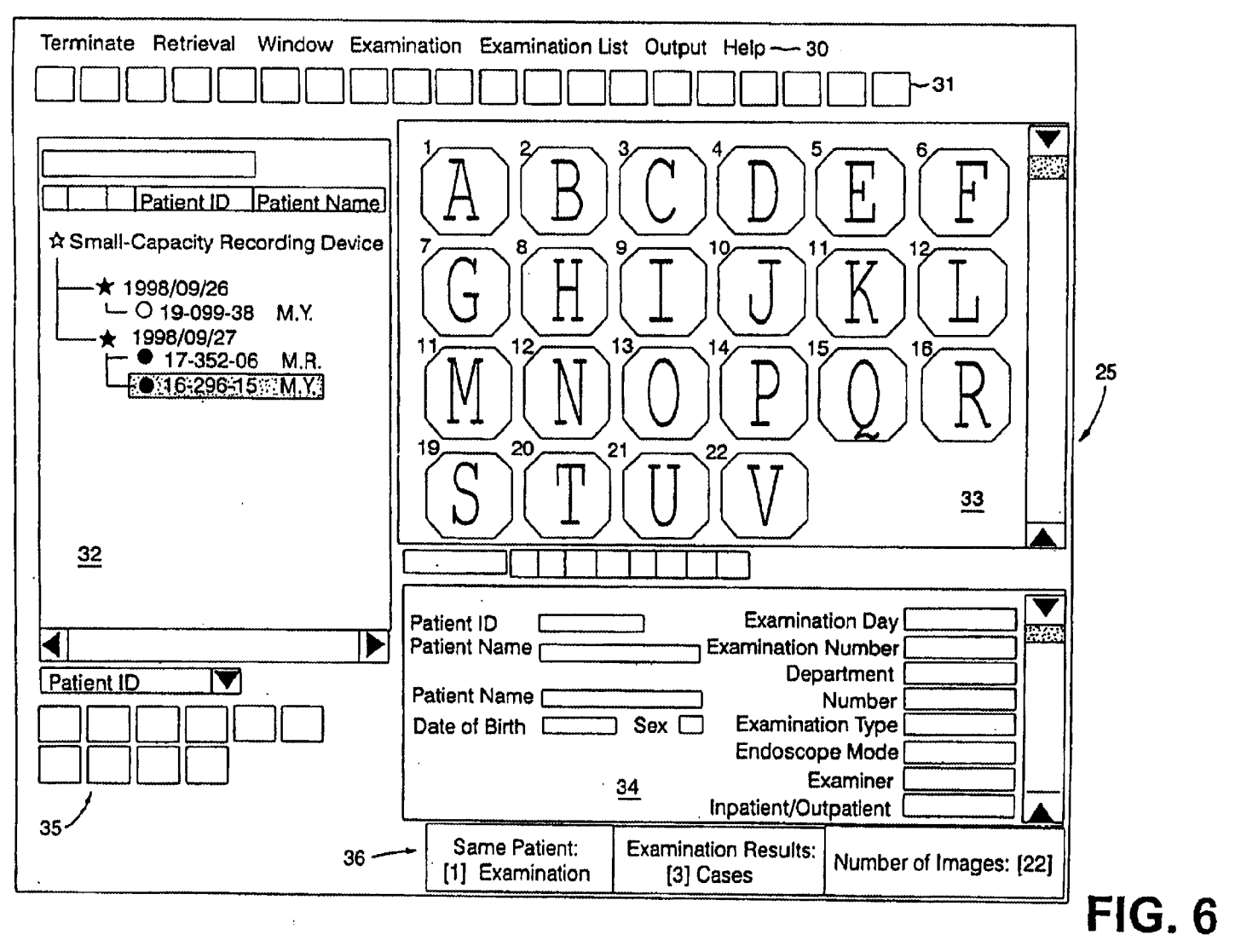
Figure 7:
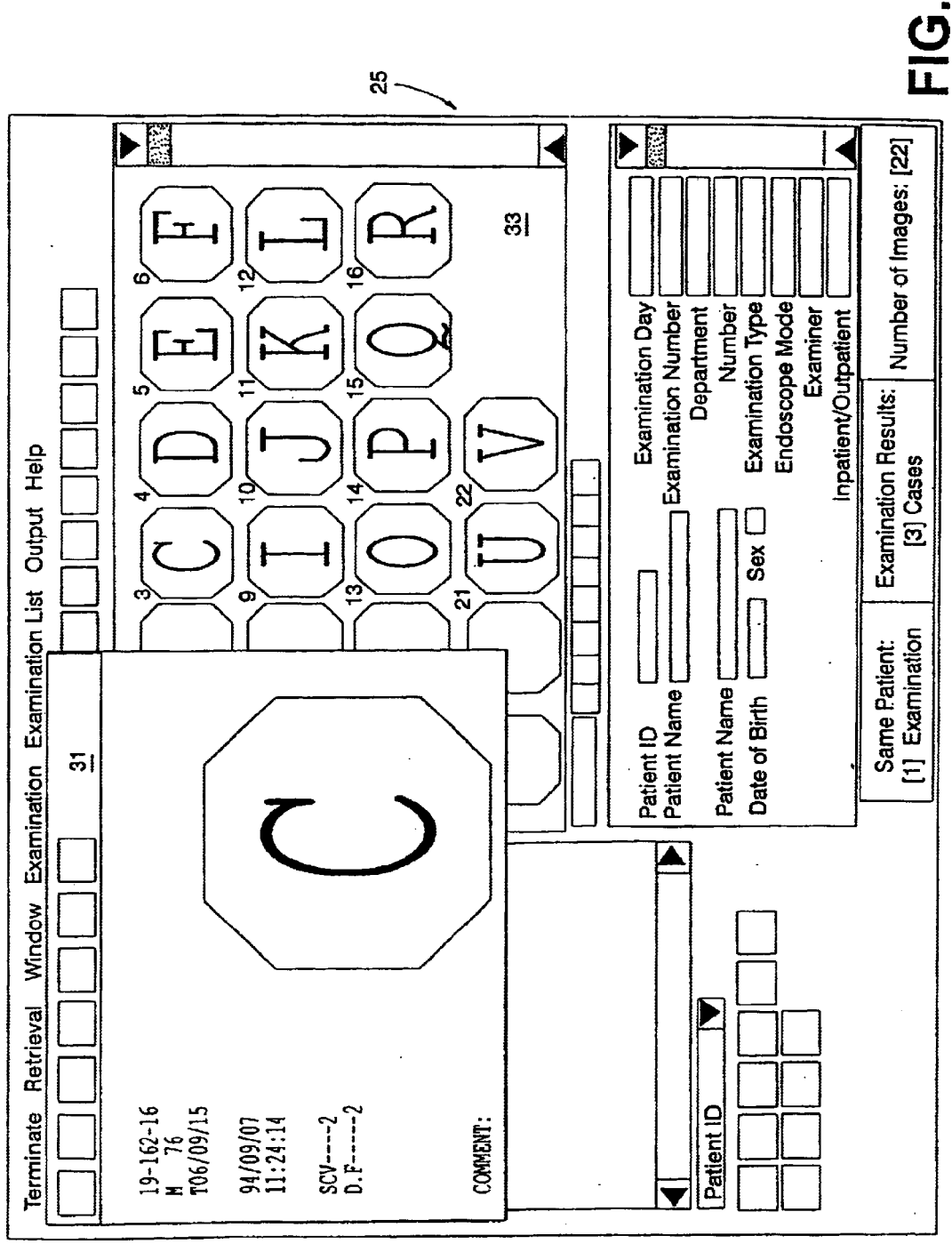
FIG. 7 is a diagram showing a second display example of the image displayed on the PC monitor of FIG. 1.

In the main screen 25 on the second PC monitor 17, if a search is performed where a keyword etc. is designated, as shown in FIG. 6, the index image of the searched images will be displayed in the image display area 33. In FIG. 7, a designated index image displayed in the image display area 33 of FIG. 6 is displayed on the main screen 25 in a larger size. Designating an index image is possible by double clicking the desired index image. Thus, in the medical image filing system 1 of this embodiment, by using the image reproducing device 16, a desired examination image can be searched, reproduced, and displayed.

Next, the reading out of an examination image beforehand will be described. As mentioned above, in the image reproducing device 16 of the present invention, it is taken into consideration to reduce time to reproduce an image which is recorded in only the large-capacity recording device 15 with a slow reproduction speed. The function to read out an image beforehand is prepared as an icon at the object copy area 35.

Figure 8:
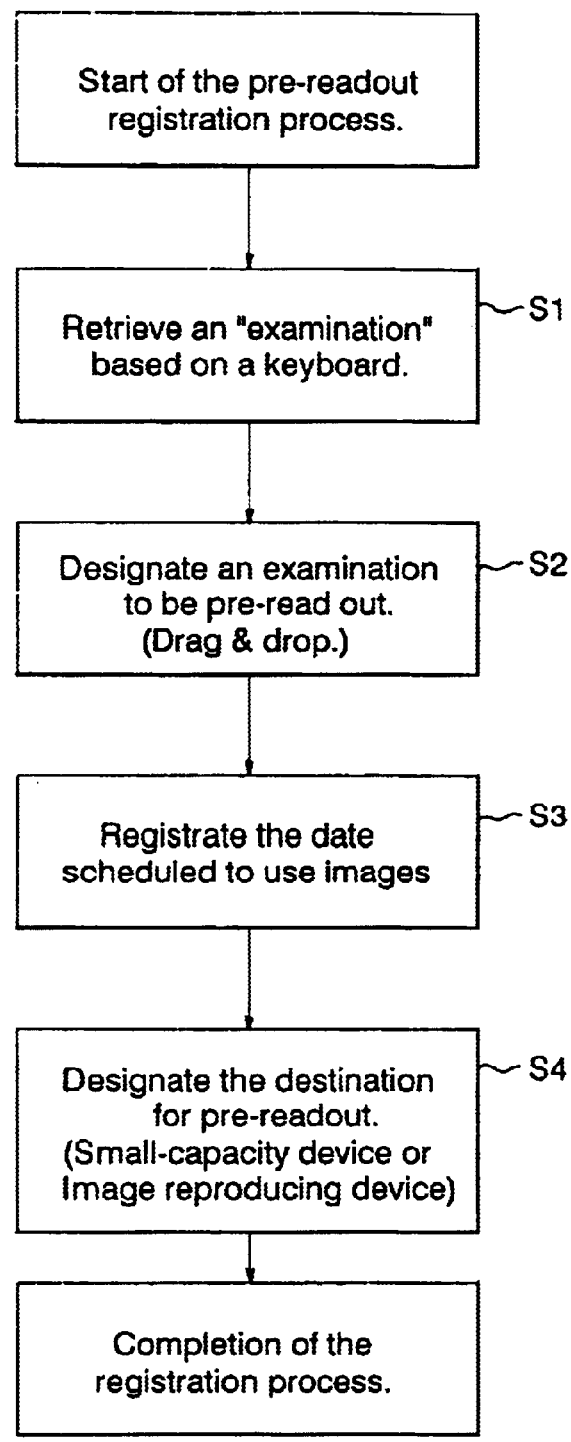
FIG. 8 is a flow chart showing the process of registration to read an image beforehand by the image reproducing means of FIG. 1.

Reading out an image beforehand is performed as follows according to the flow chart in FIG. 8. At step S1, a patient's examination data is searched by using a keyword etc. At step S2, an examination from the patient's examination data search is designated to be pre-read out. The designation is performed by dragging and dropping examination data displayed at the examination list display area 32 to and on the pre-readout registration icon 35a with a mouse 20, as shown in FIG. 9.

Examination data which requires time to display an image after instructing reproduction is recorded in the large-capacity recording device 15. Therefore, the process records a mark to know instantly whether the image remains in both the small and large-capacity recording devices 14,15, respectively, or if the image remains only in the large-capacity recording device 15.

Also, a setting allowing the reading out of designated examination data beforehand is possible. It is possible to choose by a setting whether all past examination data of a designated patient is to be read out, or only designated data. Furthermore, only new examination data or a predetermined number of examinations can also be chosen to be read out beforehand.

Figure 10:
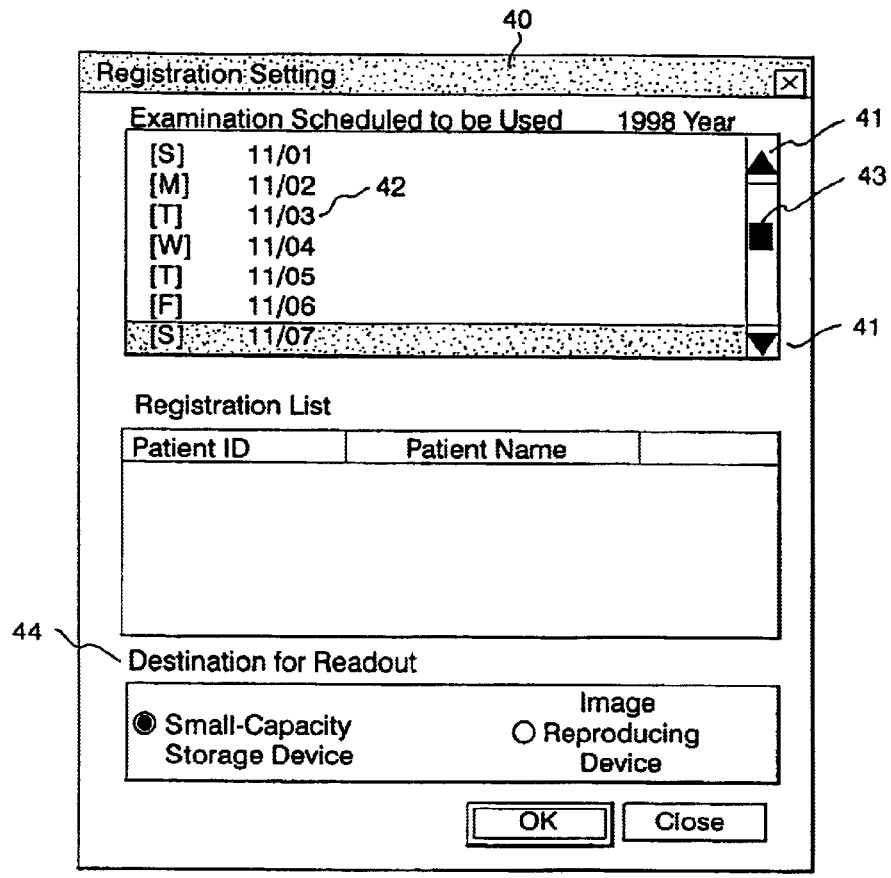
FIG. 10 is a diagram showing a second example of an image displayed on the PC monitor at the time of a registration process to read image data beforehand shown in FIG. 8.

When an examination is designated at Step S2, the registration setting window 40 shown in FIG. 10 will be opened to select a date when examination images are expected to be used at Step S3. It is possible to select by clicking the scroll buttons 41 (▼ or ▲), or double-clicking the notation of the expected date 42 for use with the mouse 20. And, it is possible to select the date of today by clicking button 43. Next, at Step S4, the destination which can store pre-read data can be selected at the read data destination 44 from the small-capacity recording device 14 and the image reproducing device 16. Images to be pre-read out can be read out to a location selected here and stored.

When the small-capacity recording device 14 is selected, and images are read out to the small-capacity recording device 14, it is possible to reproduce them with each of the plural image reproducing devices connected to LAN 5. On the other hand, since it is possible to pre-read them out from all the image reproducing devices, the number of pre-readout cases also tends to increase, therefore, the recording capacity may be quickly exhausted.

When the image reproducing device 16 is chosen, pre-read images are read out in the memory 22 of the reserved reproducing device. Therefore, although the recording capacity cannot be quickly exhausted, images cannot be reproduced with each of other reproducing devices. Since the destination of pre-read data can be selected in such a way, data can be flexibly read out in accordance with various uses. As a desirous example, it can be thought that only those examination images that may be surely retrieved or reproduced are read out to the small-capacity recording device 14, while other ones are read out to the image reproducing device 16. Thus, through the process of steps S1 through S4 as shown in FIG. 8, registration of pre-read data can be completed.

Figure 11:
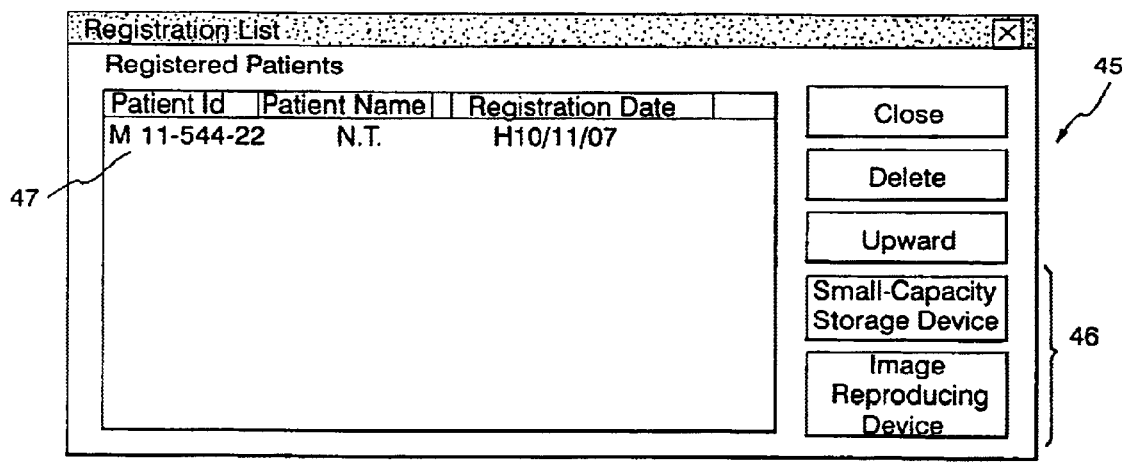
FIG. 11 is a diagram showing a third example of an image displayed on the PC monitor at the time of a registration process to read image data beforehand in FIG. 8.

When the pre-readout registration icon 35a in the object copy area 35 is double-clicked with the mouse 20, the registered patients list window 45 for the registered examination shown in FIG. 11 can be shown where data which has been reserved for pre-readout can be confirmed, or any reservation can be canceled.

A registered patients list can be shown in a different manner depending on whether the destination of pre-read data is the small-capacity recording device 14 or the image reproducing device 16 itself. In FIG. 11, the data on the patient 47 is scheduled to be pre-read out to the image reproducing device 16 selected with the button 46.

Figure 12:
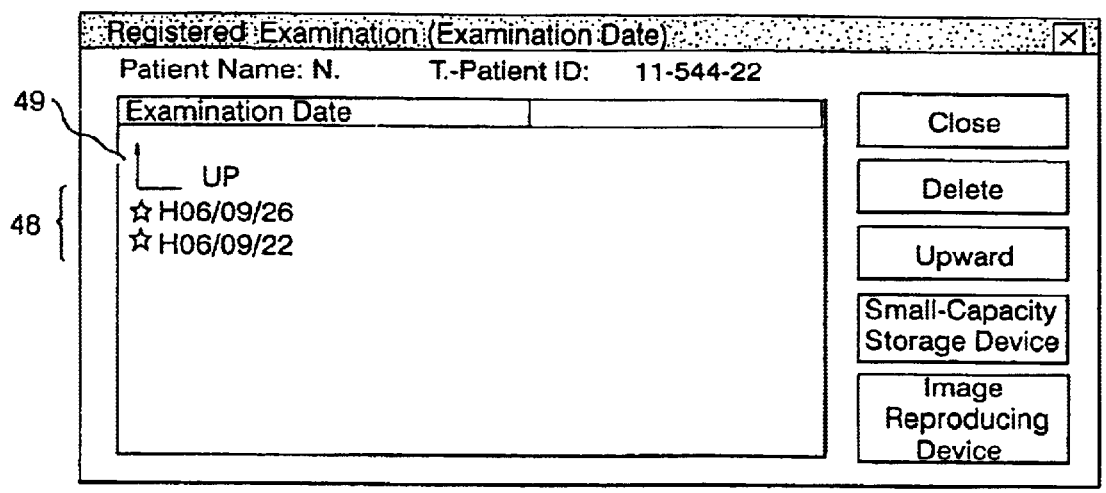
FIG. 12 is a diagram showing a fourth example of an image displayed on the PC monitor at the time of a registration process to read image data beforehand in FIG. 8.

When the name of the patient 47 displayed in the registered patients list window 45 is double-clicked with the mouse 20, all the dates 48 of those examinations for the patient whose data are to be pre-read can be displayed as shown in FIG. 12. By clicking "UP" 49, the user can return to the registered patients list window 45.

Figure 13:
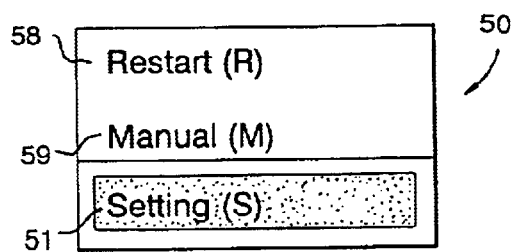
FIG. 13 is a diagram showing a fifth example of an image displayed on the PC monitor at the time of a registration process to read image data beforehand in FIG. 8.

Next, the time when data are pre-read out will be described. Pre-readout is effective in reproducing an image in the large-capacity recording device 15 whose reading speed is slower. However, when the pre-readout process is simultaneous with the usual retrieval/reproduction process, the latter may be slowed or obstructed. Therefore, it is desirable that the pre-readout process should be carried out during the time when the usual retrieval/reproduction process is not being carried out. The image reproducing device 16 of this embodiment can designate the pre-readout time. The pre-readout time can be set as follows:

(1) When the pre-readout registration icon 35a in the object copy area 35 is clicked with the mouse 20, the menu 50 as shown in FIG. 13 will be displayed.

Figure 14:
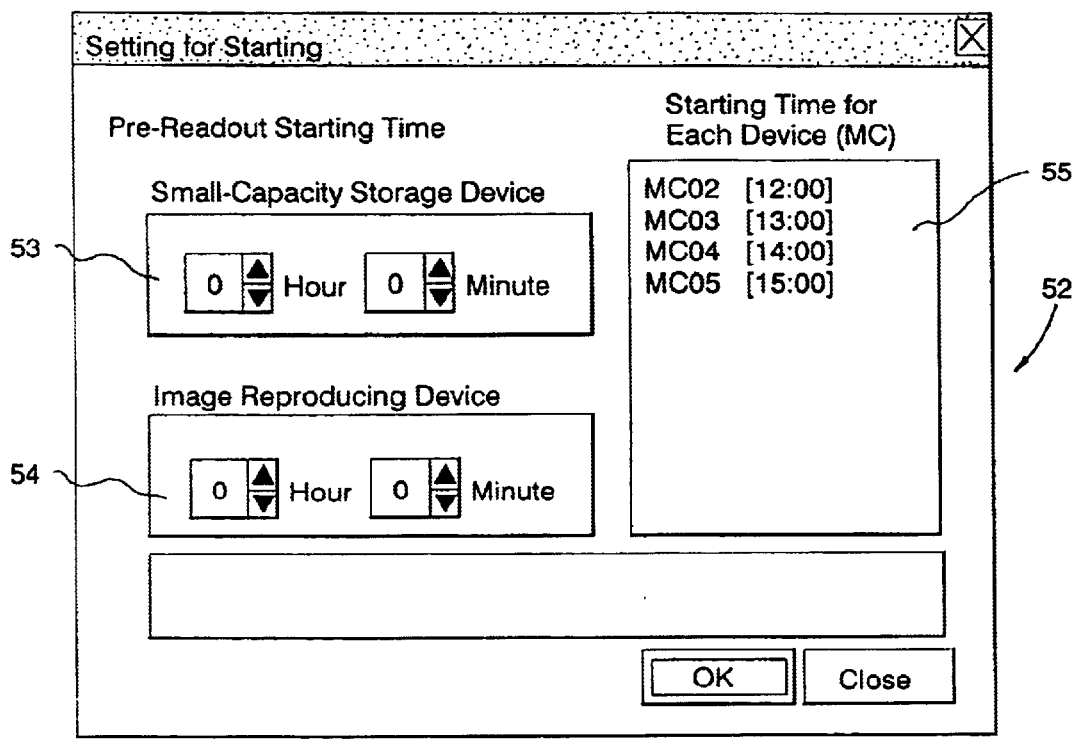
FIG. 14 is a diagram showing a sixth example of an image displayed on the PC monitor at the time of a registration process to read image data beforehand in FIG. 8.

(2) When "Setting" 51 is selected from the menu 50, the start-up setting window 52 in FIG. 14 can be opened.

(3) By clicking the up and down buttons ▼ and ▲ in the time setting area 53 for the small-capacity recording device 14, or the time setting area 54 for image reproducing-device 16 with the mouse 20, the pre-readout starting time can be set.

Since pre-readout starting times for other image reproducing devices are shown in the right column 55 of the window at this moment, it can be set so that it may not overlap with pre-readout starting times for other devices. It is also possible to restrict input so that it may not overlap with other starting times. In this case, measures can be taken, of course, so that the same time as starting times set for other image reproducing devices may not be input. Also, measures can be taken so that from the outset, the time regarded as required for the pre-readout process may be prevented from being input. Because the number of images picked up for an examination is generally given, it is possible to prevent such time as required to pre-read out preset number of images from being input.

Because the time for pre-reading an examination image can be designated in this way, the pre-readout time can be set at night so that it may not overlap with the usual retrieval/reproduction process. Moreover, because both the small-capacity recording device 14 and the image reproducing device 16 can respectively designate the pre-readout starting time, the pre-readout process can be done according to a more flexible schedule.

When a schedule for pre-readout is registered, pre-readout of examination images starts at the starting time of the previous day of the expected use day. If the image reproducing device 16 is off, however, they will not be pre-read out. Therefore, when a user tries to turn off the image reproducing device 16 of this embodiment in which a schedule for pre-readout is reserved, the notification message "A schedule for pre-readout is registered. Would you turn off the power?" will be shown to the user.

Next, the control of the device when the pre-readout process has overlapped with the usual retrieval/reproduction process, or when the pre-readout process fails for some reason will be described.

Figure 15:
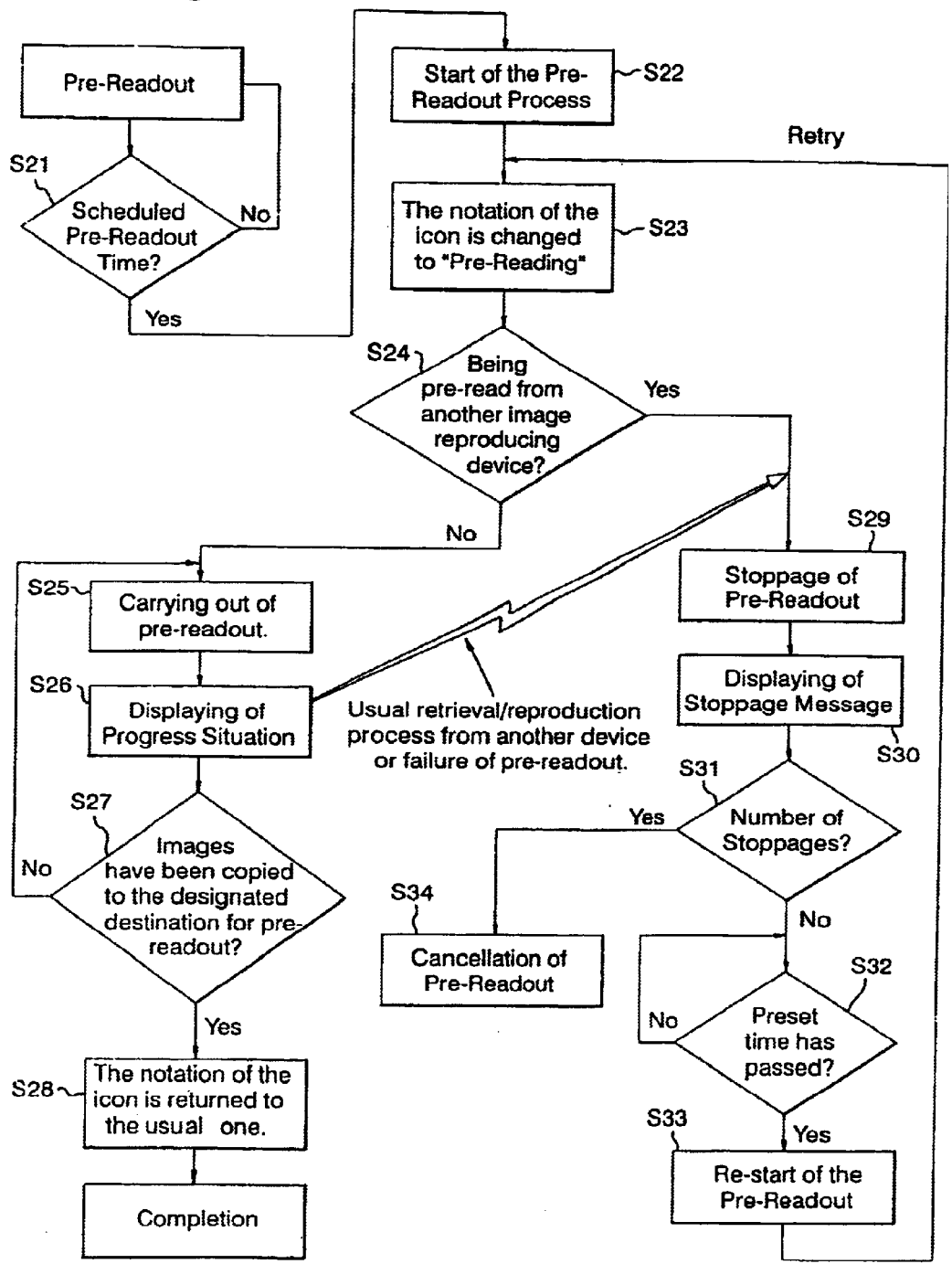
FIG. 15 is a flow chart showing the process of reading image data beforehand by the image reproducing means of FIG. 1.

As shown in FIG. 15, the scheduled pre-readout time is waited for at Step S21, and pre-readout starts at Step S22 when the scheduled pre-readout time comes. After starting pre-readout, the icon is changed to "Pre-Reading" at Step S23 to confirm whether images are being read out from another image reproducing device connected to LAN 5 at Step S24.

When images are not being read out from another image reproducing device at Step S24, pre-readout should be performed on Step S25, and the progress situation should be displayed on the second PC monitor 17 at Step S26. And, whether images have been copied to the designated destination should be confirmed at Step 27. If not, the process returns to Step S25, while if copied, the process returns the icon to the normal notation to finish the process at Step 28.

When images are being read out from another image reproducing device at Step S24, the pre-readout process is stopped at Step S29. At Step S30, a stoppage message is displayed on the second PC monitor 17. Then, at Step S31, whether the number of stoppages of the pre-readout process "n" has reached the preset value "T" should be confirmed. If not, after a lapse of a preset time at Step S32, the user can restart the pre-readout process at Step S33, and return to S23 to retry the pre-readout process. At this time, the number of stoppages of the pre-readout process "n" should be incremented at Step S33.

If it is again determined that images are being read out from another image reproducing device at Step 24, the pre-read-out process will be canceled at step S34 when the number of stoppages of the pre-readout process "n" is determined to have reached the preset value "T".

Even though it is possible to set the pre-readout time as mentioned above, it cannot be said that there is no possibility of conducting the usual retrieval/reproduction process during the time set for the pre-readout process, a wrong pre-readout time may be set, or images may be referred to at night in an emergency or for research activities. Therefore, there is some possibility that the usual retrieval/reproduction process may overlap with the pre-readout time. In such a case, priority should be given to the usual retrieval/reproduction process. As explained in the flowchart of FIG. 15, priority is given to the usual image retrieval process and the pre-readout process is stopped when the usual retrieval/reproduction process overlaps with the pre-readout time in the image reproducing device 16 of this embodiment.

Furthermore, the pre-readout process may fail for one reason or another. For example, the network cable which connects the device to LAN 5 may dislodge from the connector; there may be a contact failure; traffic is temporarily high due to some abnormality in the LAN 5; because images can't be pre-read out from plural image reproducing devices, several pre-readout processes may overlap; or, the pre-readout process may be stopped because a scheduled time overlaps with the system maintenance time of the medical image filing system. In case the pre-readout process stops or fails, it is retried T times after a lapse of the preset time. The number of and the time for retries can be changeable.

Figure 16:
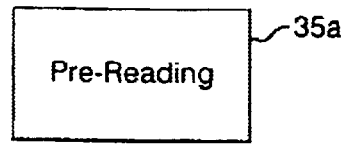
FIG. 16 is a drawing showing the indication of an icon for reading beforehand the image of FIG. 9 when reading image data beforehand is conducted.
Figure 17:
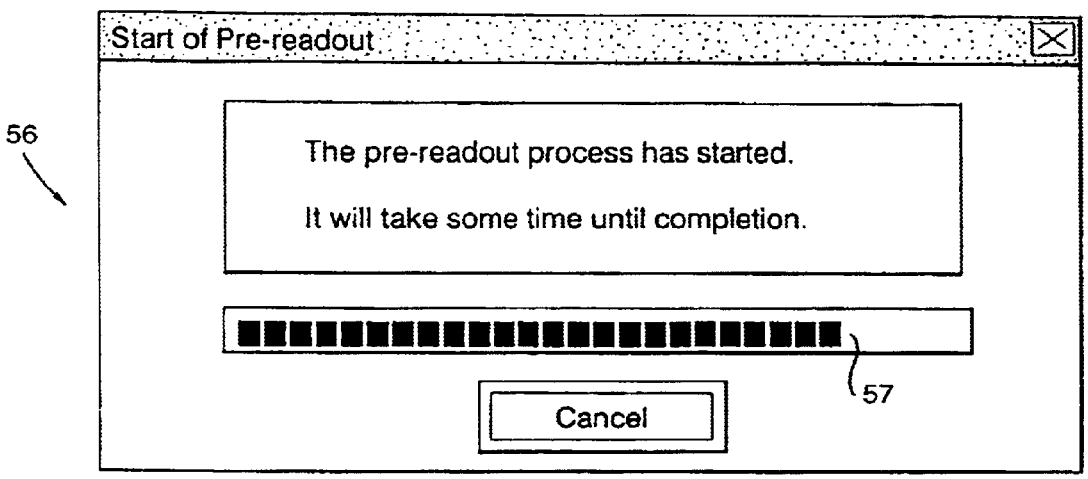
FIG. 17 is a diagram showing an example of an image displayed on the PC monitor at the process of reading image data of FIG. 15.

Next, it will be explained how the start and stoppage of the pre-readout process are indicated. When the pre-readout starting time comes on the previous day of the expected use day registered through the pre-readout registration procedure, the notation of the pre-readout registration icon 35a in the object copy area 35 will be changed to that as shown in FIG. 16, and the pre-readout window 56 as shown in FIG. 17 is opened to start the pre-readout process. The degree in progress of the pre-readout process is shown on the pre-readout window 56, preferably with a bar graph 57, by which the user can understand how the pre-readout process advances.

Figure 18:
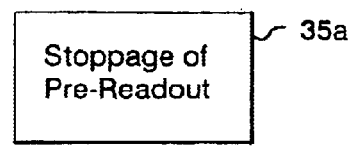
FIG. 18 is a drawing showing the indication of an icon for reading beforehand the image of FIG. 9 when reading image data beforehand is stopped.

If the pre-readout process of images from another image reproducing device or the usual image retrieval/reproduction process is advancing when the pre-readout starting time comes on the previous day of the expected use day registered through the pre-readout registration procedure, the pre-readout process will be stopped after a message "Images are being pre-read out from another image reproducing device (MC)," or "Images from another image reproducing device (MC) are being reproduced." Furthermore, the notation of the pre-readout icon in the object copy area 35 is changed to that as shown in FIG. 18, by which the user can find that the pre-readout process has been stopped.

When the pre-readout process stops, it will be automatically retried as many as the indicated preset number of times as mentioned above. If the user finds through a displayed message or changed notation of the icon that the pre-readout process has been stopped, however, he can also restart the pre-readout process by manual operation. For restarting the pre-readout process, it is sufficient to choose "Restart" 58 from the menu 50 obtained by a right click on the pre-readout registration icon 35a (see FIG. 13).

It is also possible to start the pre-readout process at a time other than the preset pre-readout starting time. In this case, "Manual" 59 should be selected from the menu 50 obtained by a right click on the pre-readout registration icon 35a in the object copy area 35 (see FIG. 13).

When "Manual" 59 is selected, all the examination images that are to be read out on that day and the next day are read out. As mentioned above, all the examination images to be read out on that day and the next day can be read out here. However, the user can make the setting such that examination images selected from the pre-readout registration list may be read out. The readout process starting with "Manual" 59 is effective when the pre-readout process has not started, for example, because the image reproducing device was off at the pre-readout starting time.

Next, it will be explained how to reproduce pre-read examination images. As shown in FIG. 19, examinations whose images have been pre-read out are shown in the examination list displaying area 32. When "Pre-readout (Small-capacity recording device)" or "Pre-readout (Image reproducing device)" is selected from the combo box 60 for selecting a retrieval medium (a storage device), examinations whose images have been pre-read out can be shown for the selected device. As for those examinations shown in such a way, images can be reproduced according to the same procedure as the usual retrieval/reproduction process, namely, images can be displayed by double-clicking the desired examination.

Pre-read images can be stored in the small-capacity recording device 14 or image reproducing device 16 itself whose retrieval/reproduction speed is very high, and reproduced at high speed. Since the memory of the small-capacity recording device 14 or that of the image reproducing device 16 is limited, however, pre-read image data cannot be stored for a long time. Therefore, after the preset number of days have passed after the expected use date of examination images, this embodiment allows them to be deleted. By doing so, the situation in which the memory is filled with pre-read images so that another pre-readout process cannot start is avoidable. Because pre-read images can remain within the preset number of days after the expected use date, it is effective, for example, in the situation where there is an insubstantial change to the use schedule, and they are actually used a few days later.

When the schedule is substantially changed or canceled, the pre-readout registration itself should be changed. However, it is effective, for example when the use day is changed without cancellation of the schedule. It is desirable for the number of preset days to be changed. Since the number of pre-read images is reduced if a quite long period is selected, care should be taken. When as a result of the pre-readout process, the memory has become filled with examination images for which the preset number of days have not yet passed after the expected use day, the message "The memory is full of pre-read images" is displayed to notify the user that no more images can be read out. In this case, the pre-readout process must be canceled, or the schedule must be changed. Or, if pre-read examination images are manually deleted, the pre-readout process can be newly carried out. Of course, if the preset number of days have passed after the expected use date, and examination images stored in the memory can be deleted, the pre-readout process can be newly performed in an automatic manner.

Since the medical image filing system 1 of the present embodiment can pre-read out required examination image data, and copy in advance and store them in the small-capacity recording device 14 or the image reproducing device 16 itself through access to the large-capacity recording device 15 as mentioned above, the time required for retrieval can be reduced.

Devices of the medical image filing system 1 are connected through LAN 5, and plural image reproducing devices 16 can be connected. In this case, if image data are pre-read out from plural image reproducing devices, and the number of pre-readout cases is increased, there is some risk that the pre-readout process may be obstructed or delayed by the usual retrieval reproduction process, for example, due to the fact that the usual retrieval/reproduction process overlaps the reserved pre-readout process. Because the pre-readout process is temporarily stopped, and retried as many as the number of preset times after a lapse of the preset time, however, the usual retrieval/reproduction process can be carried out without being delayed or obstructed.

Since the medical image filing system 1 according to the present invention can pre-read out required examination image data, and copy in advance and store them in a first recording device (small-capacity recording device) 14 or a third recording device (memory 22) of the image reproducing device 16 through access to a second recording device (large-capacity recording device) 15, the time required to retrieve or reproduce image data stored in a large-capacity recording device 15 can be reduced.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

What is claimed is:

1. A medical image filing system comprising:
   at least one image reproducing device;
   a first recording device for recording a plurality of image data from a medical image pickup device, the first recording device is not comprised in the at least one image reproducing device;
   a second recording device for recording a plurality of image data from the medical image pickup device, the second recording device having a recording speed slower and a recording capacity greater than that of the first recording device;
   a third recording device for recording a plurality of image data from the medical pickup device, the third recording device is comprised in the at least one image reproducing device and has a recording speed faster and recording capacity smaller than that of the second recording device; and
   a designating portion for allowing a user to designate one recording device from a plurality of recording devices, which plurality of recording devices includes at least the first recording device and the third recording device, the designation is for reading an image data recorded in the second recording device and recording the read data on the designated recording device before the reproduction of the image data on the at least one image reproducing device.

2. The medical image filing system of claim 1, wherein the at least one image reproducing device comprises a plurality of image reproducing devices and the medical image filing system further comprises a network for connecting each of the plurality of image reproducing devices.

3. The medical image filing system of claim 1, wherein the medical image filing system has a function to delay the copying of the designated image data from the second recording device to the designated recording device when there exists a simultaneous copying of image data within the medical image filing system.

4. The medical image filing system of claim 3, wherein the medical image filing system further has a function to restart the delayed copying of the designated image data from the second recording device to the designated recording device after the simultaneous copying is completed.

5. The medical image filing system of claim 4, wherein the delayed copying restarts through a manual indication.

6. The medical image filing system of claim 4, wherein the delayed copying restarts automatically after a lapse of a preset time.

7. The medical image filing system of claim 3, wherein the at least one image reproducing device displays a stoppage message when the copying is delayed.

8. The medical image filing system of claim 1, wherein the designating portion further accepts designation of a day and time on which the copying of the designated image data from the second recording device to the designated recording device is to be performed.

9. The medical image filing system of claim 8,
   wherein the at least one image reproducing device comprises a plurality of image reproducing devices,
   wherein the designating portion does not accept the designation of the starting time of copying which start time is already set for copying for another of the plurality of image reproducing devices.

10. The medical image filing system of claim 1,
    wherein the at least one image reproducing device comprises a plurality of image reproducing devices, and a plurality of image data can be designated for copying from the second recording device to the designated recording devices for reproduction on each of the plurality of image reproducing devices respectively;

wherein the medical image filing system has a function to stop copying of all but one of the plurality of designated image data.

11. The medical image filing system of claim 10, wherein the medical image filing system further has a function to restart the copying of at least one of the plurality of designated image data that was stopped after the copying of the one of the plurality of designated image data is completed.

12. The medical image filing system of claim 11, wherein the stopped copying restarts through a manual indication.

13. The medical image filing system of claim 11, wherein the stopped copying restarts automatically after a lapse of a preset time.

14. The medical image filing system of claim 10, wherein at least one of the plurality of image reproducing devices displays a stoppage message when the copying is stopped.

15. The medical image filing system of claim 1, wherein the designating portion further accepts designation of a day that the designated image data is to be used and the medical image filing system performs the copying on a previous day of the designated day.

16. The medical image filing system of claim 1, wherein the designation portion is embodied in the at least one image reproducing device.

17. A computer program product embodied in a computer-readable medium for reproducing a plurality of image data in a medical image filing system, the medical image filing system having first, second and third recording devices for recording the plurality of image data from a medical image pickup means, the second recording device having a recording speed slower and a recording capacity greater than that of the first recording device, the third recording device has a recording speed faster and a recording capacity smaller than that of the second image device, the computer program product comprising:

computer readable program code means for designating at least one image data from the plurality of image data recorded in the second recording device;

computer readable program code means for allowing a user to designate one recording device from a plurality of recording devices, which plurality of recording devices includes at least the first recording device and the third recording device, for copying of the designated image data from the second recording device to the designated recording device; and computer readable program code means for copying the at least one designated image data from the second recording device to the designated recording device.

18. The computer program product of claim 17, further comprising computer readable program code means for delaying the copying of the designated image data in the second recording device to the designated recording device when there exists a simultaneous copying of image data within the system.

19. The computer program product of claim 18, further comprising computer readable program code means for restarting the copying of the designated image data in the second recording device to the designated recording device after the simultaneous copying is completed.

20. The computer program product of claim 17, further comprising computer readable program code means for designating a day and time to copy the designated image data in the second recording device to the designated first or third recording device.

21. The computer program product of claim 17, further comprising computer readable program code means for designating a day that the designated image data is to be used and performing the copying on a previous day of the designated day.

22. A medical image filing system comprising:

at least one image reproducing device;

a first recording device for recording a plurality of image data from a medical image pickup device, the first recording device is not comprised in the at least one image reproducing device;

a second recording device for recording a plurality of image data from the medical image pickup device, the second recording device having a recording speed slower and a recording capacity greater than that of the first recording device;

a pre-readout time designating portion for designating a pre-readout time for reading image data stored in the second recording device to copy the image data to the first recording device, wherein a pre-readout process is stopped when the pre-readout time of the pre-readout process overlaps with a period of a readout process on which the pre-readout time is not designated.

* * * * *